US010396293B2

(12) United States Patent
Nicht et al.

(10) Patent No.: US 10,396,293 B2
(45) Date of Patent: Aug. 27, 2019

(54) ELECTRONIC OR OPTOELECTRONIC DEVICE COMPRISING AN ANCHORED THIN MOLECULAR LAYER, PROCESS FOR ITS PREPARATION AND COMPOUND USED THEREIN

(71) Applicant: Novaled GmbH, Dresden (DE)

(72) Inventors: Sylvia Nicht, Dresden (DE); Jan Blochwitz-Nimoth, Dresden (DE); Björn Lüssem, Kent, OH (US); Karl Leo, Dresden (DE); Axel Fischer, Dresden (DE)

(73) Assignee: Novaled GmbH, Dresden (DE)

( * ) Notice: Subject to any disclaimer, the term of this patent is extended or adjusted under 35 U.S.C. 154(b) by 505 days.

(21) Appl. No.: 14/912,705

(22) PCT Filed: Aug. 19, 2014

(86) PCT No.: PCT/EP2014/067608
§ 371 (c)(1),
(2) Date: Feb. 18, 2016

(87) PCT Pub. No.: WO2015/024919
PCT Pub. Date: Feb. 26, 2015

(65) Prior Publication Data
US 2016/0211461 A1 Jul. 21, 2016

(30) Foreign Application Priority Data

Aug. 19, 2013 (EP) ..................................... 13180827

(51) Int. Cl.
*C07D 249/04* (2006.01)
*H01L 51/00* (2006.01)
(Continued)

(52) U.S. Cl.
CPC ........ *H01L 51/0067* (2013.01); *C07D 249/04* (2013.01); *H01L 51/105* (2013.01);
(Continued)

(58) Field of Classification Search
CPC ...................... H01L 2251/301; H01L 51/0067
See application file for complete search history.

(56) References Cited

U.S. PATENT DOCUMENTS 6,878,469 B2  4/2005 Yoon et al.
2008/0203905 A1  8/2008 Je et al.
(Continued)

FOREIGN PATENT DOCUMENTS

EP       2 412 674 A1    2/2012
WO       2009/107596 A1  9/2009
(Continued)

OTHER PUBLICATIONS

Lu, et al., ChemPhysChem, 2006, vol. 7, pp. 854-862. (Year: 2006).*
Hertler, et al., Journal of the American Chemical Society, 1962, pp. 3387-3393. (Year: 1962).*
PCT International Search Report and Written Opinion for PCT/EP2014/067608 dated Sep. 9, 2014 (8 pages).
(Continued)

*Primary Examiner* — Sadie White
(74) *Attorney, Agent, or Firm* — Eversheds Sutherland (US) LLP

(57) ABSTRACT

Electronic and optoelectronic devices are provided that may include at least one inorganic surface covered at least partly by an organic layer. The organic layer may include a compound having at least one anchor group anchoring the compound to the inorganic surface, at least one functional moiety, and at least one methylidenyl group. Compounds and methods for manufacturing electronic and optoelectronic devices also are provided.

16 Claims, 5 Drawing Sheets

(51) Int. Cl.
*H01L 51/10* (2006.01)
*H01L 51/50* (2006.01)
*H01L 51/05* (2006.01)
*H01L 51/56* (2006.01)

(52) U.S. Cl.
CPC ...... *H01L 51/5088* (2013.01); *H01L 51/0545* (2013.01); *H01L 51/0558* (2013.01); *H01L 51/56* (2013.01); *H01L 2251/301* (2013.01)

(56) References Cited

U.S. PATENT DOCUMENTS

| | | |
|---|---|---|
| 2010/0090588 A1 | 4/2010 | Yokoyama et al. |
| 2010/0134052 A1* | 6/2010 | Gough .................. B82Y 30/00 315/363 |
| 2010/0203663 A1 | 8/2010 | Hotta et al. |
| 2011/0024728 A1 | 2/2011 | Burroughes et al. |
| 2012/0049171 A1 | 3/2012 | Fukuda et al. |

FOREIGN PATENT DOCUMENTS

| | | |
|---|---|---|
| WO | 2012/001358 A1 | 1/2012 |
| WO | 2012/127863 A1 | 9/2012 |

OTHER PUBLICATIONS

Kafer, "Characteristic and Optimization of Growth and Electronic Structure of Organic Thin Films for Applications in Organic Electronics," Department of Physical Chemistry I at the Ruhr-University Bochum, Germany, 2008, 207 pages.

Tang et al., "Organic Electroluminescent Diodes," Appl. Phys. Lett., 1987, 51(12):913-915.

Duan et al., "Controlling the Recombination Zone of White Organic Light Emitting Diodes with Extremely Long Lifetimes," Adv. Funct. Mater., 2011, 21:3540-3545.

Lih et al., "4.3:A Phosphorescent Active-Matrix OLED Display Driven by Amorphous Silicon Backplane," SID 03 Digest, 2003, pp. 14-17.

Tsujimura et al., "4.1:A 20-Inch OLED Display Driven by Super-Amorphous-Silicon Technology," SID 03 Digest, 2003, pp. 6-9.

Chinese Office Action for CN Application No. 201480052052.1 dated Oct. 11, 2017 (10 pages).

European Office Action for EP Application No. 13180827.1 dated Nov. 13, 2017 (5 pages).

Elgemeie et al., "Novel Cyanoketene N,S-Acetals and Pyrazole Derivatives Using Potassium 2-Cyanoethylene-1-thiolates," Synethtic Communications, 2007, 37:2827-2834.

* cited by examiner

| 13 |
|----|
| 12 |
| 14 |
| 11 |
| 10 |

| 27 |
|----|
| 26 |
| 25 |
| 24 |
| 23 |
| 22 |
| 28 |
| 21 |
| 20 |

ELECTRONIC OR OPTOELECTRONIC DEVICE COMPRISING AN ANCHORED THIN MOLECULAR LAYER, PROCESS FOR ITS PREPARATION AND COMPOUND USED THEREIN

CROSS REFERENCE TO RELATED APPLICATIONS

This application is a U.S. national stage application of PCT/EP2014/067608, filed Aug. 19, 2014, which claims priority to European Application No. 13180827.1, filed Aug. 19, 2013. The contents of these applications are hereby incorporated by reference.

The present invention relates to an electronic or optoelectronic device comprising an anchored thin molecular layer. The present invention also relates to a process for preparation of the electronic or optoelectronic device and to compounds suitable therefore.

BACKGROUND OF THE INVENTION

Since the demonstration of efficient organic light emitting diodes (OLEDs) by Tang et al. in 1987 (C. W. Tang et al., Appl. Phys. Lett. 51 (12), 913 (1987)), OLEDs developed from promising candidates to high-end commercial displays. An OLED comprises a sequence of thin layers substantially made of organic materials. The layers typically have a thickness in the range of 1 nm to 5 µm. The layers are usually formed either in vacuum by means of vapor deposition or from a solution, for example by means of spinning on or printing.

OLEDs emit light after the injection of charge carriers in the form of electrons from the cathode and in form of holes from the anode into organic layers arranged in between. The charge carrier injection is effected on the basis of an applied external voltage, the subsequent formation of excitons in a light emitting zone and the radiative recombination of those excitons. At least one of the electrodes is transparent or semitransparent, in the majority of cases in the form of a transparent oxide, such as indium tin oxide (ITO), or a thin metal layer.

Flat displays based on OLEDs can be realized both as a passive matrix and as an active matrix. In the case of passive matrix displays, the image is generated by for example, the lines being successively selected and an image information item selected on the columns being represented. However, such displays are restricted to a size of approximately 100 lines for technical construction reasons.

Displays having high information content require active driving of the sub-pixels. For this purpose, each sub-pixel is driven by a circuit having transistors, a driver circuit. The transistors are usually designed as thin film transistors (TFT). Full color displays are known and typically used in mp3-players, digital photo cameras, and mobile phones; earliest devices were produced by the company Sanyo-Kodak. In this case, active matrices made of polysilicon which contain the respective driver circuit for each sub-pixel are used for OLED displays. An alternative to polysilicon is amorphous silicon, as described by J.-J. Lih et al., SID 03 Digest, page 14 et seq. 2003 and T. Tsujimura, SID 03 Digest, page 6 et seq. 2003. Another alternative is to use transistors based on organic semiconductors.

Examples of OLED layer stacks used for displays are described by Duan et al (DOI: 10.1002/adfm.201100943). Duan shows blue OLEDs and white OLEDs. He modified the devices with one light emitting layer to a double and triple light emitting layer, achieving a longer lifetime at the cost of a more complex device stack. Other state-of-the art stacks are disclosed in U.S. Pat. No. 6,878,469 B2, WO 2009/107596 A1 and US 2008/0203905.

Generally, in electronic and/or optoelectronic devices requiring charge transfer through phase interfaces, minimization of contact resistances occurring on these interfaces is required, to achieve low operating voltages, high energetic efficiency and low heat load. Charge injection layers comprising organic or inorganic electrical n- or p-dopants are known as a means allowing enhanced charge injection into adjacent semiconducting layers.

Small-molecule organic dopants that can be deposited at relatively low temperatures e.g. by vacuum thermal evaporation (VTE) and/or by solution processing like dip coating, spin coating or jet printing are already used in mass OLED and display production. Yet, there is significant disadvantage that on the interface between the organic charge injecting layer consisting of small molecules and the adjacent organic layer, poorly reproducible processes can occur during deposition of the adjacent organic layer. In certain cases, especially if the adjacent layer is deposited by solution processing, special precautions are necessary for avoiding complete destruction of the previously deposited injection layer.

Monomolecular organic layers chemically anchored to an inorganic substrate are known and studied preferentially as so called self-assembling monolayers (SAMs). A good introduction into SAM thermal stability and SAM application in organic field effect transistors (OFETs) can be found e.g. in a Thesis by Daniel Käfer, Ruhr-University Bochum, 2008, http://www-brs.ub.ruhr-uni-bochum.de/netahtml/HSS/Diss/KaeferDaniel/diss.pdf, particularly on pages 130-162. Attempts to prepare electronic devices with an oriented layer of dipole molecules on the interface between an inorganic electrode and an adjacent organic layer are known also from patent literature, e.g., from WO2012/001358 and the documents cited therein. Despite the steady progress in the field, there is still an unmet demand for highly effective and stable hole injecting layers.

Only very few examples of molecular layers comprising true strong electrical p-dopants that could create holes e.g. in triarylamines (compound class that is currently most widely used in organic electronic devices as hole transporting matrices) is known. Quinoid systems substituted with electron withdrawing groups (EWGs) like tetrafluoro-tetracyanoquinodimethane (F4TCNQ) or hexaazatriphenylene (HAT) derivatives substituted with EWGs like hexaazatriphenylene hexacarbonitrile (HATCN) were successfully vacuum deposited on noble metal surfaces and strong influence of these layers on the photoelectron spectra was experimentally proven. Nevertheless, it is not yet known whether those layers could be deposited also from solution and whether p-dopants like F4TCNQ or HATCN containing amine and/or nitrile groups having only weak Lewis basicity are anchored to the metal surface strong enough to sustain a solution processing of a further organic layer on top of the molecular charge injecting layer.

It is an object of the present invention to provide an electronic or optoelectronic device wherein the hole injecting layer overcomes disadvantages of the prior art, preferably devices wherein the hole injection layer comprises a strong electrical p-dopant capable to inject holes effectively into currently used triarylamine hole transporting matrices and wherein the hole injecting layer is anchored strong enough to sustain solution processing of an adjacent organic layer. Another object of the invention is to provide a process that enables the desired electronic or optoelectronic devices with a strongly anchored and effective hole injecting layer. Yet another object of the invention is to provide new compounds enabling the desired devices and their manufacture.

SUMMARY OF THE INVENTION

The object is achieved by an electronic or optoelectronic device as provided herein, a process as provided herein, and a compound as provided herein.

Especially, the object is achieved by an electronic or optoelectronic device comprising at least one inorganic surface covered at least partly by an organic layer, wherein the organic layer comprises a compound comprising
  i) at least one anchor group anchoring the compound to the inorganic surface,
  ii) at least one functional moiety comprising
    a) an aromatic heterocycle containing at least one nitrogen atom in an aromatic ring or
    b) an aromatic or heteroaromatic ring substituted with at least one secondary or tertiary amine group,
  iii) at least one methylidenyl group,
  wherein at least one of the nitrogen atoms comprised in or bound to an aromatic ring of the functional moiety is directly attached by a single bond to the methylidenyl group, and wherein the anchor group is attached to the functional moiety either directly or by a spacer.

It is preferred that the methylidenyl group directly attached by a single bond to the nitrogen atom comprised in or bound to an aromatic ring of the functional moiety is substituted. Also preferably, the methylidenyl group is not a part of a ring. More preferably, the substituent on the methylidenyl group is an electron withdrawing group or another functional moiety comprising at least one anchor group and
  a) an aromatic heterocycle containing at least one nitrogen atom in an aromatic ring or
  b) an aromatic or heteroaromatic ring substituted with at least one secondary or tertiary amine group,
  wherein the other functional moiety is attached through a single bond between the methylidenyl group and nitrogen atom comprised in or bound to an aromatic ring comprised in this functional moiety. More preferably, the electron withdrawing group is cyano group.

Preferably, the inorganic surface is a metal surface. More preferably, the metal surface comprises at least one metal selected from the 8, 9, 10. or 11. group of the Periodic Table. Even more preferably, the metal surface comprises as a main component a metal selected from Cu, Ag, Au, Pd or Pt. Also preferably, the anchor group comprises at least one chalcogen atom selected from S, Se, Te having the oxidation degree (-II), (-I) or 0. It is further preferred that the anchor group is selected from —SH and —$S_x$—, wherein x is an integer selected from 1, 2, 3, 4 and 5.

Preferably, the anchor group is directly attached to the nitrogen containing aromatic ring or to the amine-substituted aromatic or heteroaromatic ring of the functional moiety. Also preferably, the functional moiety is a five membered nitrogen containing aromatic ring. More preferably, the functional moiety is selected from azole, diazole, triazole and tetrazole. Also preferably, the functional moiety is substituted with at least one electron withdrawing group. It is preferred that the electron withdrawing group is independently selected from —F, —Cl, —CN, halogenated alkyl, halogenated aryl, halogenated heteroaryl. It is further preferred that the halogenated alkyl, aryl and/or heteroaryl is a perhalogenated alkyl, aryl and/or heteroaryl. Even more preferably, the perhalogenated alkyl, aryl and/or heteroaryl is a perfluorinated alkyl, aryl and/or heteroaryl. Optionally, one or more hydrogen and/or halogen atom(s) on any halogenated or perhalogenated aryl and/or heteroaryl may be replaced with cyano group(s).

Preferably, the methylidenyl group is conjugated with at least one pi-bond of another conjugated pi-electron system. More preferably, the other conjugated pi-electron system is substituted with at least one electron withdrawing group and/or is electron withdrawing itself. Preferred examples of the other conjugated pi-electron system are quinoid, truxequinone or radialene pi-electron systems. It is preferred that the electron withdrawing group is independently selected from —F, —Cl, —CN, halogenated alkyl, halogenated aryl, halogenated heteroaryl. It is further preferred that the halogenated alkyl, aryl and/or heteroaryl is a perhalogenated alkyl, aryl and/or heteroaryl. Even more preferably, the perhalogenated alkyl, aryl and/or heteroaryl is a perfluorinated alkyl, aryl and/or heteroaryl. Optionally, one or more hydrogen and/or halogen atom(s) on any halogenated or perhalogenated aryl and/or heteroaryl may be replaced with cyano group(s).

The object is further achieved by process for manufacturing an electronic or optoelectronic device according to this invention, comprising the steps
  ia) providing a precursor compound comprising
    I. an anchor group for anchoring the precursor compound to an inorganic surface,
    II. a functional moiety precursor comprising
      a) an aromatic heterocycle containing at least one NH unit in the ring or
      b) an aromatic or heteroaromatic ring substituted with at least one primary or secondary amine,
      wherein the anchor group is attached to the functional moiety precursor either directly or by a spacer
  iia) modifying an inorganic surface by anchoring the precursor compound to the inorganic surface,
  iiia) optionally removing any excess of the precursor compound, preferably by washing the modified inorganic surface obtained in step ii),
  iva) reacting a compound having at least one methylidene group that is substituted with at least one electron withdrawing substituent with at least one of the NH unit of
    ivaa) the aromatic heterocycle containing at least one NH unit or
    ivab) the primary or secondary amine group of the aromatic or heteroaromatic ring substituted with at least one primary or secondary amine
    comprised in the precursor compound anchored to the modified inorganic surface obtained in step ii) or iii),
  va) optionally, removing unreacted compound having at least one methylidene group that is substituted with at least one electron withdrawing substituent, preferably by washing the modified inorganic surface obtained in step iv)
  or,
  ib) providing a precursor compound comprising
    I. an anchor group for anchoring the precursor compound to an inorganic surface,
    II. a functional moiety precursor comprising
      a) an aromatic heterocycle containing at least one NH unit in the ring or
      b) an aromatic or heteroaromatic ring substituted with at least one primary or secondary amine, wherein the anchor group is attached to the functional moiety precursor either directly or by a spacer iib) mixing the precursor compound with a compound having at least one methylidene group that is substituted with at least one electron withdrawing substituent, iiib) modifying an inorganic surface by contacting it with the mixture created in step iib), ivb) optionally, removing compounds that have not anchored to the inorganic surface, preferably by washing the modified inorganic surface obtained in step iiib).

It is preferred that the electron withdrawing substituent is cyano group. More preferably, the methylidene group that is substituted with at least one electron withdrawing substituent is a dicyanomethylidene group.

Preferably, the inorganic surface is a metal surface. More preferably, the metal surface comprises at least one metal selected from the 8, 9, 10. or 11. group of the Periodic Table. Even more preferably, the metal surface comprises as a main component a metal selected from Cu, Ag, Au, Pd or Pt. Also preferably, the anchor group comprises at least one chalcogen atom selected from S, Se, Te having the oxidation degree (-II), (-I) or 0. It is further preferred that the anchor group is selected from —SH and —$S_x$—, wherein x is an integer selected from 1, 2, 3, 4 and 5.

Preferably, the anchor group is directly attached to the nitrogen containing aromatic ring or to the amine-substituted aromatic or heteroaromatic ring of the functional moiety. Also preferably, the functional moiety is a five membered nitrogen containing aromatic ring. More preferably, the functional moiety is selected from azole, diazole, triazole and tetrazole. Also preferably, the functional moiety is substituted with at least one electron withdrawing group. It is preferred that the electron withdrawing group is independently selected from —F, —Cl, —CN, halogenated alkyl, halogenated aryl, halogenated heteroaryl. It is further preferred that the halogenated alkyl, aryl and/or heteroaryl is a perhalogenated alkyl, aryl and/or heteroaryl. Even more preferably, the perhalogenated alkyl, aryl and/or heteroaryl is a perfluorinated alkyl, aryl and/or heteroaryl. Optionally, one or more hydrogen and/or halogen atom(s) on any halogenated or perhalogenated aryl and/or heteroaryl may be replaced with cyano group(s).

Preferably, the methylidene group that is substituted with at least one electron withdrawing substituent is conjugated with at least one pi-bond of another conjugated pi-electron system. More preferably, the other conjugated pi-electron system is substituted with at least one electron withdrawing group and/or is electron withdrawing itself. Preferred examples of the other conjugated pi-electron system are quinoid, truxequinone or radialene pi-electron systems. It is preferred that the electron withdrawing group is independently selected from —F, —Cl, —CN, halogenated alkyl, halogenated aryl, halogenated heteroaryl. It is further preferred that the halogenated alkyl, aryl and/or heteroaryl is a perhalogenated alkyl, aryl and/or heteroaryl. Even more preferably, the perhalogenated alkyl, aryl and/or heteroaryl is a perfluorinated alkyl, aryl and/or heteroaryl. Optionally, one or more hydrogen and/or halogen atom(s) on any halogenated or perhalogenated aryl and/or heteroaryl may be replaced with cyano group(s).

The object is further achieved by compound, comprising:
i) at least one functional moiety comprising
   a) an aromatic heterocycle containing at least one nitrogen atom in an aromatic ring or
   b) an aromatic or heteroaromatic ring substituted with at least one secondary or tertiary amine group,
ii) at least one anchor group comprising at least one chalcogen atom selected from S, Se, Te in the oxidation degree (-II), (-I) or 0, the anchor group being attached to the functional moiety either directly or by a spacer,
iii) at least one methylidenyl group,
wherein at least one nitrogen atom comprised in or bound to an aromatic ring of the functional moiety is directly attached by a single bond to the methylidenyl group.

It is preferred that the methylidenyl group directly attached by a single bond to the nitrogen atom comprised in or bound to an aromatic ring of the functional moiety is substituted. Also preferably, the methylidenyl group is not a part of a ring. More preferably, the substituent on the methylidenyl group is an electron withdrawing group or another functional moiety comprising at least one anchor group and
   a) an aromatic heterocycle containing at least one nitrogen atom in an aromatic ring or
   b) an aromatic or heteroaromatic ring substituted with at least one secondary or tertiary amine group,
wherein the other functional moiety is attached through a single bond between the methylidenyl group and nitrogen atom comprised in or bound to an aromatic ring comprised in this functional moiety. More preferably, the electron withdrawing group is cyano group.

Preferably, the anchor group is selected from —SH and —$S_x$—, wherein x is an integer selected from 1, 2, 3, 4 and 5.

Preferably, the anchor group is directly attached to the nitrogen containing aromatic ring or to the amine-substituted aromatic or heteroaromatic ring of the functional moiety. Also preferably, the functional moiety is a five membered nitrogen containing aromatic ring. More preferably, the functional moiety is selected from azole, diazole, triazole and tetrazole. Also preferably, the functional moiety is substituted with at least one electron withdrawing group. It is preferred that the electron withdrawing group is independently selected from —F, —Cl, —CN, halogenated alkyl, halogenated aryl, halogenated heteroaryl. It is further preferred that the halogenated alkyl, aryl and/or heteroaryl is a perhalogenated alkyl, aryl and/or heteroaryl. Even more preferably, the perhalogenated alkyl, aryl and/or heteroaryl is a perfluorinated alkyl, aryl and/or heteroaryl. Optionally, one or more hydrogen and/or halogen atom(s) on any halogenated or perhalogenated aryl and/or heteroaryl may be replaced with cyano group(s).

Preferably, the methylidenyl group is conjugated with at least one pi-bond of another conjugated pi-electron system. More preferably, the other conjugated pi-electron system is substituted with at least one electron withdrawing group and/or is electron withdrawing itself. Preferred examples of the other conjugated pi-electron system are quinoid, truxequinone or radialene pi-electron systems. It is preferred that the electron withdrawing group is independently selected from —F, —Cl, —CN, halogenated alkyl, halogenated aryl, halogenated heteroaryl. It is further preferred that the halogenated alkyl, aryl and/or heteroaryl is a perhalogenated alkyl, aryl and/or heteroaryl. Even more preferably, the perhalogenated alkyl, aryl and/or heteroaryl is a perfluorinated alkyl, aryl and/or heteroaryl. Optionally, one or more hydrogen and/or halogen atom(s) on any halogenated or perhalogenated aryl and/or heteroaryl may be replaced with cyano group(s).

ADVANTAGEOUS EFFECT OF THE INVENTION

The invention provides not yet available devices comprising very thin molecular layers comprising covalently bound strong electrical dopants and anchored to an inorganic electrode surface by a strong ionic, covalent or coordination bond. Both the ionic, covalent or coordinative anchoring and covalent binding prevent deterioration of the prepared thin molecular layer in the subsequent step of the device preparation and improve device reproducibility and performance.

DETAILED DESCRIPTION OF THE INVENTION

Device Architecture

Organic Electronic Devices

Figures 1, 2, 3A:
FIG. 1 shows a schematic illustration of the layer structure of a diode comprising the inventive anchored thin molecular layer.
FIG. 2 shows a schematic illustration of the layer structure of an OLED comprising the inventive anchored thin molecular layer.
FIGS. 3a and 3b show schematic illustrations of the layer structure of (FIG. 3a) bottom gate and (FIG. 3b) top gate OFETs comprising the inventive anchored thin molecular layer.

FIG. 1 illustrates a first embodiment of an inventive organic electronic device in the form of an organic Schottky-diode. In FIG. 1, 10 is a substrate, 11 is a first electrode, 12 is an organic semiconductor layer, 14 is the inventive thin molecular layer anchored to the first electrode, 13 is a second electrode.

Preferably, 11 is an anode, 13 is a cathode and 14 acts as HIL (hole injection layer), decreasing the operating voltage of the whole device by decreasing the potential barrier for the charge injection from anode in the semiconductor layer 12.

Nevertheless, it was surprisingly found that the inventive thin molecular layer improves the diode according to FIG. 1 even if it is operated with the opposite polarity. In this variant of the first embodiment, 11 is a cathode and 13 is an anode. From the FIG. 6 as discussed below, it is clearly seen that the inventive thin molecular layer markedly decreases the leakage current through the diode. It is supposed that this unexpected secondary effect of the inventive layer may consist in its favourable influence on the morphology of the adjacent semiconductor layer 12.

The organic diode can be more complex, e.g. the organic semiconductor layer 12 can comprise two sublayers, a hole conducting sublayer 12a and an electron conducting sublayer 12b (not shown in FIG. 1).

FIG. 2 represents a second embodiment of the inventive organic electronic device in the form of an organic light emitting diode (OLED). Here, 20 is a substrate, 21 is a first electrode, 22 is a hole transport layer, 23 is an electron blocking layer, 24 is a light emission layer, 25 is a hole blocking layer, 26 is an electron transport layer, 27 is the second electrode. 28 is the inventive thin molecular layer anchored to the first electrode.

Preferably, 21 is an anode, 27 is a cathode and 28 acts as HIL (hole injection layer), decreasing the operating voltage of the whole device by decreasing the potential barrier for the charge injection from anode in the hole transporting layer 22.

FIG. 3a illustrates a third embodiment of the inventive device in the form of a bottom gate/bottom source-drain OFET as a representative of an organic thin film transistor (OTFT). The OTFT comprises a substrate 30a, a gate electrode layer 31a, an insulator material 32a, a source 33a and a drain 34a, or alternatively, a drain 33a and a source 34a, an organic semiconductor material 35a and the inventive thin molecular layer 36a.

Figure 3B:
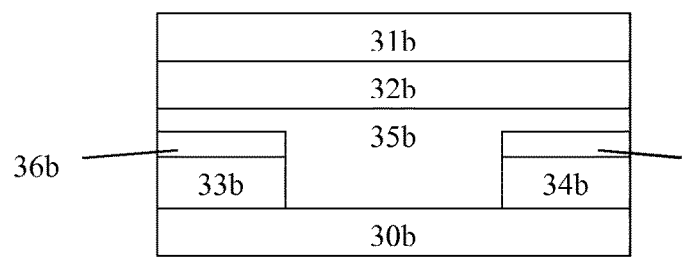

FIG. 3b illustrates a fourth embodiment of the inventive device in form of a top gate/bottom source drain OFET. The OFET comprises a substrate 30b, a gate electrode layer 31b, a insulator material 32b, a source 33b and a drain 34b, or alternately a drain 33b and a source 34b, an organic semiconductor material 35b and the inventive thin molecular layer 36b.

In the variants of the third and fourth embodiment of the invention that are shown on the FIGS. 3a and 3b, the inventive thin molecular layer is anchored to both the source and the drain electrodes. In these variants, the polarity of the transistor is not decisive. Irrespective whether 33a or 33b is the source and 34a or 34b the drain or oppositely, the inventive thin molecular layer is supposed to improve the hole injection on the source electrode and the morphology of the semiconductor layer on the drain electrode, improving favourably the whole current-voltage characteristics of the device as shown on the FIG. 7 discussed below. This variant of the invention is especially preferred from the manufacturing point of view, because anchoring the inventive thin molecular layer to both electrodes 33a and 34a as well as to both electrodes 33b and 34b is the simplest possible procedure.

Of course, it is also possible provide transistors having the inventive thin molecular layer 36 anchored only to one of the electrodes 33 and 34. Again, the inventive layer is supposed to work the same way as discussed above: if attached to the drain electrode, it is supposed that there prevails the positive effect of its smoothness on the morphology of the adjacent semiconductor layer, whereas if attached to the source electrode, it is supposed that there prevails its effect as hole injecting layer, despite the positive influence on the morphology of the adjacent semiconductor layer is also very likely.

Material Properties—Energy Levels

A method to determine the ionization potentials (IP) is the ultraviolet photo spectroscopy (UPS). It is usual to measure the ionization potential for solid state materials; however, it is also possible to measure the IP in the gas phase. Both values are differentiated by their solid state effects, which are, for example the polarization energy of the holes that are created during the photo ionization process. A typical value for the polarization energy is approximately 1 eV, but larger discrepancies of the values can also occur. The IP is related to beginning of the photoemission spectra in the region of the large kinetic energy of the photoelectrons, i.e. the energy of the most weakly bounded electrons. A related method to UPS, the inverted photo electron spectroscopy (IPES) can be used to determine the electron affinity (EA). However, this method is less common. Electrochemical measurements in solution are an alternative to the determination of solid state oxidation ($E_{ox}$) and reduction ($E_{red}$) potential. An adequate method is for example the cyclo-voltammetry. A simple rule is used very often for the conversion of red/ox potentials into electron affinities and ionization potential: IP=4.8 eV+e*$E_{ox}$ (vs. Ferrocen/Ferrocenium) and EA=4.8 eV+e*$E_{red}$ (vs. Ferrocen/Ferrocenium) respectively (see B. W. Andrade, Org. Electron. 6, 11 (2005)). Processes are known for the correction of the electrochemical potentials in the case other reference electrodes or other redox pairs are used (see A. J. Bard, L. R. Faulkner, "Electrochemical Methods: Fundamentals and Applications", Wiley, 2. Ausgabe 2000). The information about the influence of the solution used can be found in N. G. Connelly et al., Chem. Rev. 96, 877 (1996). It is usual, even if not exactly correct to use the terms "energy of the HOMO" E(HOMO) and "energy of the LUMO" E(LUMO) respectively as synonyms for the ionization energy and electron affinity (Koopmans Theorem). It has to be taken in consideration, that the ionization potentials and the electron affinities are given in such a way that a larger value represents a stronger binding of a released or respectively of an absorbed electron. The energy scale of the molecular orbitals (HOMO, LUMO) is opposed to this. Therefore, in a rough approximation, is valid: IP=−E(HOMO) and EA=E(LUMO). The given potentials correspond to the solid-state potentials.

Substrate

It can be flexible or rigid, transparent, opaque, reflective, or translucent. The substrate should be transparent or translucent if the light generated by the OLED is to be transmitted through the substrate (bottom emitting). The substrate may be opaque if the light generated by the OLED is to be emitted in the direction opposite of the substrate, the so called top-emitting type. The display can also be fully transparent. The substrate can be either arranged adjacent to the cathode or anode.

Electrodes

The electrodes must provide a certain amount of conductivity, being preferentially conductors. In an OLED, at least one of the electrodes must be semi-transparent or transparent to enable the light transmission to the outside of the device. In OLEDs generally, typical electrodes are layers or a stack of layer, comprising metal and/or transparent conductive oxide. Other possible electrodes are made of thin busbars (e.g. a thin metal grid) wherein the spaces between the busbars is filled (coated) with a transparent material with a certain conductivity, such as graphene, carbon nanotubes, doped organic semiconductors, etc.

In a direct current circuit, the electrodes in a diode can be assigned as an anode and a cathode. Anode is the electrode attached to the positive pole of the used voltage source, whereas cathode is attached to the negative pole. In one mode, the anode is the electrode closest to the substrate, which is called non-inverted structure. In another mode, the cathode is the electrode closest to the substrate, which is called inverted structure.

In OLEDs, typical materials for the anode are ITO and metals of 8.-11. group of the Periodic Table. Cu, Ag, Au, Pd and Pt are the preferred metals. Typical materials for the cathode are Mg:Ag (10 vol. % Mg), Ag, ITO, Al. Mixtures and multilayer are also possible.

Preferably, the OLED cathode comprises a metal selected from Ag, Al, Mg, Ba, Ca, Yb, In, Zn, Sn, Sm, Bi, Eu, Li, more preferably from Al, Mg, Ca, Ba and even more preferably selected from Al or Mg. Preferred is also a cathode comprising an alloy of Mg and Ag.

Hole-Transporting Layer (HTL)

In OLEDs, HTL is a layer comprising a large gap semiconductor responsible to transport holes from the anode or holes from a CGL to the light emitting layer (LEL). The HTL is comprised between the anode and the LEL or between the hole generating side of a CGL and the LEL. The HTL can be mixed with another material, for example a p-dopant, in which case it is said the HTL is p-doped. The HTL can be comprised by several layers, which can have different compositions. P-doping the HTL lowers its resistivity and avoids the respective power loss due to the otherwise high resistivity of the undoped semiconductor. The doped HTL can also be used as optical spacer, because it can be made very thick, up to 1000 nm or more without significant increase in resistivity.

Suitable hole transport materials (HTM) can be, for instance HTM from the diamine class, where a conjugated system is provided at least between the two diamine nitrogens. Examples are N4,N4'-di(naphthalen-1-yl)-N4,N4'-diphenyl-[1,1'-biphenyl]-4,4'-diamine (HTM1), N4,N4,N4",N4"-tetra([1,1'-biphenyl]-4-yl)-[1,1':4',1"-terphenyl]-4,4"-diamine (HTM2). The synthesis of diamines is well described in literature; many diamine HTMs are readily commercially available.

Hole-Injecting Layer (HIL)

Is a layer which facilitates the injection of holes from the anode or from the hole generating side of a CGL into an adjacent HTL. Typically, the HIL is a very thin layer (thickness<10 nm). The hole injection layer can be a pure layer of p-dopant and can be about 1 nm thick. When the HTL in a device is doped, an HIL may not be necessary, since the injection function is already provided by the HTL. The inventive thin molecular layer may serve as HIL. In this embodiment, the inventive thin molecular layer is anchored to an inorganic anode surface with a strong ionic, covalent or coordination bond. As the inventive HIL comprises a covalently bound strong p-dopant providing a good hole injection, the HTL in the inventive devices may be both doped or undoped.

Formation of the Inventive Thin Molecular Layer

The reaction of primary and secondary aliphatic amines with TCNQ was described by Heftier et al in J. Am. Chem. Soc. 1962, pages 3387-3393. As the alkyl substituents of aliphatic amines are electron donating groups, a person skilled in the art can expect that replacing one or two strongly electron withdrawing cyano groups in TCNQ with electron donating amine groups will significantly decrease the oxidation ability of the resulting amino-cyano quinodimethane compounds. For more powerful p-dopant F4TCNQ, the authors of the present invention confirmed this assumption by means of quantum-chemical computations. These computations, when expanded on the aromatic amines or amines comprising their secondary nitrogen atoms as a part of a heterocyclic system, have shown that the undesired increase of the LUMO levels for the expected substitution derivatives should be significantly lower in comparison with the aliphatic amines. However, significant uncertainty regarding sufficient reactivity of electron deficient aromatic amines and/or nitrogen heterocycles remained. Moreover, an additional uncertainty about expected reaction course raises when an electron deficient amine is further substituted with an anchoring group for its attachment to an inorganic electrode surface. Typical thiol, selenol, oligosulfide and similar known anchor groups for noble metal surfaces, comprising one or more chalcogen atom(s) in a low oxidation state like -II, -I or zero are also known as strong nucleophiles. The skilled person would have expected that these chalcogen groups could easily replace the easily leaving strongly electron withdrawing groups like cyano groups in the starting compounds comprising at least one methylidene group substituted with at least one such easily leaving electron withdrawing group. This undesired reaction course would have formed products with both deactivated anchor groups and LUMO levels deteriorated for the hole injection into current hole transporting materials.

When mixing a 4,4'-bis(1,2,3-triazolyl)disulfide (TAD) as a model precursor compound comprising a disulfide anchor group with F4TCNQ or F6TCNNQ as model p-dopants comprising a quinoid pi-electron systems having low LUMO levels caused by their multiple substitution with halogen and cyano electron withdrawing groups, substantially no desired substitution reaction was indeed observed.

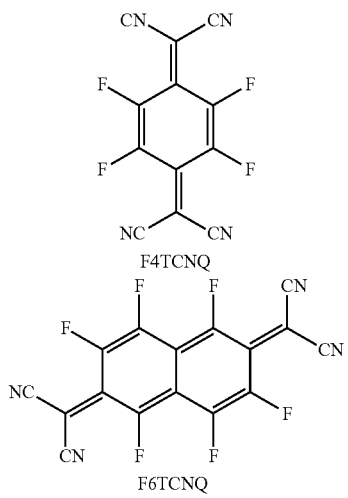

Surprisingly, when the mixing took place in presence of a noble metal surface or when TAD was previously brought in the contact with a noble metal surface and subsequently mixed with the model dopant, the reaction resulting into covalent binding of the dopant and its strong anchoring to the metal surface took place practically immediately. Further investigation has proven the preserved hole injecting ability of the formed molecular surface layers and thus revealed the technical potential of the fortunate synergy among the supposed anchoring through the chalcogen containing anchor group and activation of an amine nitrogen with prevailing $sp^2$ character in terms of reaction kinetics to enable favourable and quick binding of the p-dopant without substantial deterioration of its doping/hole injecting ability.

It is to be understood that electron withdrawing group (EWG) is any group having positive (meta and/or para) sigma value in the Hammett equation as taught in the physical organic chemistry textbooks, see also http://en.wikipedia.org/wiki/Hammett_equation.

Based on the properties of the devices comprising the inventive thin molecular layers as shown in the examples below, it is supposed that the inventive thin molecular layers have essentially the SAM character.

Light-Emitting Layer (LEL)

The light emitting layer in an OLED must comprise at least one emission material and can optionally comprise additional layers. If the LEL comprises a mixture of two or more materials the charge carrier injection can occur in different materials for instance in a material which is not the emitter, or the charge carrier injection can also occur directly into the emitter. Many different energy transfer processes can occur inside the LEL or adjacent LELs leading to different types of emission. For instance excitons can be formed in a host material and then be transferred as singlet or triplet excitons to an emitter material which can be singlet or triplet emitter which then emits light. A mixture of different types of emitter can be provided for higher efficiency. Mixed light can be realized by using emission from an emitter host and an emitter dopant.

The best performance enhancement is achieved with blue fluorescent emitters.

In OLEDs, blocking layers can be used to improve the confinement of charge carriers in the LEL, these blocking layers are further explained in U.S. Pat. No. 7,074,500 B2.

Electron-Transporting Layer (ETL)

In an OLED, ETL is a layer comprising a large gap semiconductor responsible to transport electrons from the cathode or electrons from a CGL to the light emitting layer (LEL). The ETL is comprised between the anode and the LEL or between the electron generating side of a CGL and the LEL. The ETL can be mixed with another material, for example a n-dopant, in which case it is said the ETL is n-doped. The ETL can be comprised by several layers, which can have different compositions. n-doping the ETL lowers its resistivity and avoids the respective power loss due to the otherwise high resistivity of the undoped semiconductor. The doped ETL can also be used as optical spacer, because it can be made very thick, up to 1000 nm or more without significant increase in resistivity.

Hole blocking layers and electron blocking layers can be employed as usual. In a preferred mode of the invention, the LEL has a very low HOMO and an EBL is not necessary. That is because the recombination of charge carriers with light emission is close or at the HTL/LEL interface.

Electron-Injecting Layer (EIL)

Several different techniques for providing EILs can be used. Some of those techniques are explained below: the device can comprise a buffer layer between the cathode and the ETL. This buffer layer can provide protection against the cathode deposition or metal diffusion from the cathode. Sometimes this buffer layer is named as buffer or as injection layer. Another kind of injection layer is a layer comprising an n-dopant between the ETL and the cathode. This layer can be a pure layer of n-dopant which is typically less than 5 nm thick, typically only about 1 nm thick. The use of the strong donor (n-dopant) as injection layer provides lower voltages and higher efficiency in the device. If the ETL is n-doped, then the injection layer may not be necessary. Other kinds of injection layers are: metal doped organic layer, typically using alkali metals; thin layer of a metal complexes (such as lithium quinolate (LiQ, used in examples of the present application as D1)), inorganic salts (such as LiF, NaCl, etc).

Other layers with different functions can be included, and the device architecture can be adapted as known by the skilled in the art.

Charge Generation Layer (CGL)

The OLED can comprise a CGL which can be used in conjunction with an electrode as inversion contact, or as connecting unit in stacked OLEDs. A CGL can have the most different configurations and names, examples are pn-junction, connecting unit, tunnel junction, etc. Best examples are pn junctions as disclosed in US 2009/0045728 A1, US 2010/0288362 A1. Metal layers and or insulating layers can also be used.

Stacked OLEDs

When the OLED comprises two or more LELs separated by CGLs, the OLED is named a stacked OLED, otherwise it is named a single unit OLED. The group of layers between two closest CGLs or between one of the electrodes and the closest CGL is named a electroluminescent unit (ELU). Therefore a stacked OLED can be described as anode/ELU$_1$/ {CGL$_X$/ELU$_{1+X}$}$_X$/cathode, wherein x is a positive integer and each CGL$_X$ or each ELU$_{1+X}$ can be equal or different. The CGL can also be formed by the adjacent layers of two ELUs as disclosed in US2009/0009072 A1. Further stacked OLEDs are explained e.g. in US 2009/0045728 A1, US 2010/0288362 A1, and references therein.

Deposition of Organic Layers

Organic semiconducting layers of the inventive electronic devices can be deposited by known techniques, such as vacuum thermal evaporation (VTE), organic vapour phase deposition, laser induced thermal transfer, spin coating, blade coating, slot dye coating, inkjet printing, etc. The inventive thin molecular layer is preferably prepared by solution process according to the invention.

Electrical Doping

The most reliable and at the same time efficient OLEDs are OLEDs comprising doped layers. By electrically doping hole transport layers with a suitable acceptor material (p-doping) or electron transport layers with a donor material (n-doping), respectively, the density of charge carriers in organic solids (and therefore the conductivity) can be increased substantially. Additionally, analogous to the experience with inorganic semiconductors, some applications can be anticipated which are precisely based on the use of p- and n-doped layers in a component and otherwise would be not conceivable. The use of doped charge-carrier transport layers (p-doping of the hole transport layer by admixture of acceptor-like molecules, n-doping of the electron transport layer by admixture of donor-like molecules) in organic light-emitting diodes is, e.g., described in US 2008/203406 and U.S. Pat. No. 5,093,698.

The present invention can be used in addition or in combination with electrical doping of organic semiconducting layers. This electrical doping can also be called redox-doping or charge transfer doping. It is known that the doping increases the density of charge carriers of a semiconducting matrix towards the charge carrier density of the undoped matrix.

US2008227979 discloses in detail the doping of organic transport materials, with inorganic and with organic dopants. Basically, an effective electronic transfer occurs from the dopant to the matrix increasing the Fermi level of the matrix. For an efficient transfer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than +0.3 eV.

Typical examples of doped hole transport materials are: copper phthalocyanine (CuPc), which HOMO level is approximately −5.2 eV, doped with tetrafluoro-tetracyano-quinonedimethane (F4TCNQ), which LUMO level is about −5.2 eV; zinephthalocyanine (ZnPc) (HOMO=−5.2 eV) doped with F4TCNQ; a-NPD (N,N'-Bis(naphthalen-1-yl)-N,N-bis(phenyl)-benzidine) doped with F4TCNQ. a-NPD doped with 2,2'-(perfluoronaphthalene-2,6-diylidene)dimalononitrile (PD1). a-NPD doped with 2,2',2"-(cyclopropane-1,2,3-triylidene)tris(2-(p-cyanotetrafluorophenyl)acetonitrile) (PD2).

Typical examples of doped electron transport materials are: fullerene C60 doped with acridine orange base (AOB); perylene-3,4,9,10-tetracarboxylic-3,4,9,10-dianhydride (PTCDA) doped with leuco crystal violet; 2,9-di(phenanthren-9-yl)-4,7-diphenyl-1,10-phenanthroline doped with tetrakis (1,3,4,6,7,8-hexahydro-2H-pyrimido[1,2-a]pyrimidinato) ditungsten (II) (W$_2$(hpp)$_4$); naphthalene tetracarboxylic acid di-anhydride (NTCDA) doped with 3,6-bis-(dimethyl amino)-acridine; NTCDA doped with bis (ethylene-dithio)tetrathiafulvalene (BEDT-TTF).

MATERIALS

In OLEDs, preferred emission ranges are:

Blue emission having a peak between 440 nm and 490 nm.

Yellow emission having a peak between 550 nm and 590 nm.

Green emission having a peak between 500 and 540 nm.

Red emission having a peak between 600 and 700 nm.

Known emitter dopants can be used in the invention.

Preferred Emitters

Exemplary fluorescent red emitter dopants are diindenoperylene compounds such as e.g.: 5,10,15,20-tetraphenyl-benzo[ghi]benzo[5,6]indeno[1,2,3-ed]benzo[5,6]indeno[1,2,3-lm]perylene; 5,10,15,20-tetraphenyl-7,8-dihydrobenzo[5,6]indeno[1,2,3-cd]benzo[5,6]indeno[1,2,3-lm]perylene; 1,2,3,4,9,10,11,12-octaphenyl-6,7-dihydrodiindeno[1,2,3-cd:1',2',3'-lm]perylene.

Exemplary fluorescent orange or yellow emitters are 5,6,11,12-tetraphenyltetracene; 5,6,11,12-tetra(naphthalen-2-yl)tetracene; 2,8-di-tert-butyl-5,6,11,12-tetrakis(4-(tert-butyl)phenyl)tetracene;

Green fluorescent emitter dopants can be selected, for example, from quinacridones, coumarin, and others, examples are: quinolino[2,3-b]acridine-7,14(5H,12H)-dione; 3,10-difluoroquinolino[2,3-b]acridine-7,14(5H,12H)-dione; 5,12-diphenylquinolino[2,3-b]acridine-7,14(5H,12H)-dione; 3-(benzo[d]oxazol-2-yl)-7-(diethylamino)-2H-chromen-2-one; 7-(diethylamino)-3-(4,6-dimethylbenzo[d]thiazol-2-yl)-2H-chromen-2-one; 10-(benzo[d]thiazol-2-yl)-1,1,7,7-tetramethyl-2,3,6,7-tetrahydro-1H-pyrano[2,3-f]pyrido[3,2,1-ij]quinolin-11(5H)-one; 10-(4,6-di-tert-butylbenzo[d]thiazol-2-yl)-1,1,7,7-tetramethyl-2,3,6,7-tetrahydro-1H-pyrano[2,3-f]pyrido[3,2,1-ij]quinolin-11 (5H)-one.

Exemplary fluorescent blue emitter dopants are: 9-(naphthaten-1-yl)-10-(naphthalen-2-yl)anthracene; (Z)-6-mesityl-N-(6-mesitylquinolin-2(1H)-ylidene)quinolin-2-amine-BF2 complex; bis[2-[4-[N,N-diarylamino]phenyl]vinyl]biphenyl; 6,6'-(1,2-ethenediyl)bis(N-2-naphthalenyl-N-phenyl-2-naphthalenamine); 2,5,8,11-tetra-tert-butyl-1,10-dihydroperylene;

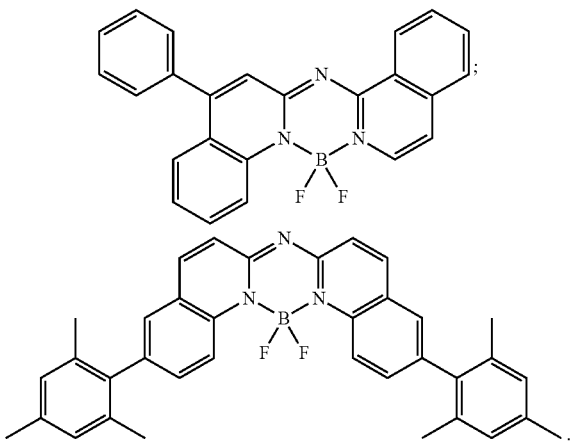

Suitable red phosphorescent emitter dopants are disclosed in US2011057559 on pages 33-35, table 1, titled "red dopants", which is incorporated herein by reference. Suitable green phosphorescent emitter dopants are disclosed in US2011057559 on pages 35-38, table 1, titled "green dopants", which is incorporated herein by reference. Suitable blue phosphorescent emitter dopants are disclosed in US2011057559 on pages 38-41, table 1, titled "blue dopants", and compounds from claim 30, which table and claim are incorporated herein by reference.

Suitable host materials for fluorescent emitters are, among others, anthracene derivatives substituted at the 9 and 10 positions, for example 9,10-di-(2-naphthyl)anthracene, 9-(1-naphthyl)-10-(2-naphthyl)-anthracene, compounds in US2005089717 A1, compounds AH1, AH2, AH3, AH4, AH5, AH6, AH7, AH8 as disclosed in pages 11-12 in US2008/0268282 A1.

Particular suitable host materials for red phosphorescent dopants are disclosed in US2011057559 on pages 28-29, table 1, titled "red host", which is incorporated herein by reference. Particular suitable host materials for green phosphorescent dopants are disclosed in US2011057559 on pages 29-32, table 1, titled "green host", which is incorporated herein by reference. Particular suitable host materials for blue phosphorescent dopants are disclosed in US2011057559 on pages 32-33, table 1, titled "blue host", which is incorporated herein by reference.

Many of the emitter dopants and hosts described above are commercially available, for example from Luminescence Technology Corp, TW or from Sun Fine Chem, KR (SFC).

Preferred Additional Materials

Donors as Electrical (Redox) Dopants

In one mode of the invention, the ETL is doped with n-dopants which are strong donors or donor precursors. Typical n-dopants are: alkaline metals like Li or Cs or alkaline earth metals like Ba, tetrathianaphthacene, [Ru(terpy)2]0; rhodamine B; pyronin B chloride; acridine orange base; leuco crystal violet; 2,2'-diisopropyl-1,1',3,3'-tetramethyl-2,2',3,3',4,4',5,5',6,6',7,7'-dodecahydro-1H,1'H-2,2-bibenzo[d]imidazole; 4,4',5,5'-tetracyclohexyl-1,1',2,2',3,3'-hexamethyl-2,2',3,3'-tetrahydro-1H,1'H-2,2'-bisimidazole (NDOP1); 2,2'-diisopropyl-4,4',5,5'-tetrakis(4-methoxyphenyl) 1,1',3,3'-tetramethyl-2,2',3,3'-tetrahydro-1H,1'H-2,2'-bisimidazole; 2-isopropyl-1,3-dimethyl-2,3,6,7-tetrahydro-1H-5,8-dioxa-1,3-diaza-cyclopenta[b]-naphthene; bis-[1,3-dimethyl-2-isopropyl-1,2-dihydro-benzimidazolyl-(2)]; tetrakis(1,3,4,6,7,8-hexahydro-2H-pyrimido[1,2-a]pyrimidinato)ditungsten(II) (W$_2$(hpp)$_4$); 2,2'-diisopropyl-4,5-bis(2-methoxyphenyl)-4',5'-bis(4-methoxyphenyl)-1,1',3,3'-tetramethyl-2,2',3,3'-tetrahydro-1H,1'H-2,2'-bisimidazole; 2,2'-diisopropyl-4,5-bis(2-methoxyphenyl)-4',5'-bis(3-methoxyphenyl)-1,1',3,3'-tetramethyl-2,2',3,3'-tetrahydro-1H,1'H-2,2'-bisimidazole (see for example, patent publications US 2005/0040390, US 2009/0212280, and US 2007/0252140).

The molar ratio of the used redox dopant or its precursor to the doped matrix is usually less than 1:1, so that there is no excess n-dopant in the layer (the ":" can be read as a division sign, so that "less" means a smaller value. Preferably the doping ratio is less than 1:4, more preferably less than 1:10 and more than 1:10000.

Alternatively, the ETL comprises a metal salt like cesium carbonate or cesium phosphate or a metal complex according to Formula III

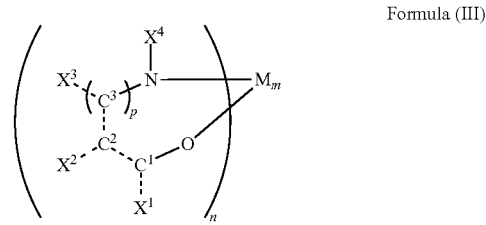

Formula (III)

wherein M is an alkali metal or an alkaline earth metal atom, $C^1$, $C^2$ and $C^3$ are carbon atoms and $X^1$-$X^4$ in formula (III) are independently selected from H, $C_1$-$C_{20}$-hydrocarbyl group optionally comprising up to three heteroatoms, $C_1$-$C_{20}$-alkyl or branched $C_4$-$C_{20}$-alkyl, $C_3$-$C_{20}$-cycloalkyl, alkenyl with $C_2$-$C_{20}$, alkinyl with $C_2$-$C_{20}$, aryl or heteroaryl, p=0 or 1, m and n are integers independently selected to provide a neutral charge on the complex, the hydrocarbyl groups optionally comprising up to three heteroatoms may form with each other a cyclic structure, at least one of sequences $X^1$—$C^1$—$C^2$—$X^2$, and $X^3$—$C^3$—N—$X^4$ is part of a fused or nonfused saturated, nonsaturated, aromatic or heteroaromatic cyclic or polycyclic system and dashed lines represent bonds which have saturated (single) or unsaturated (double) character according to saturation and/or unsaturation of the rings in which they occur.

Preferably is p=0 and $X^1$—$C^1$—$C^2$—$X^2$, and $X^3$—$C^3$—N—$X^4$ are part of a substituted or unsubstituted quinoline structure. Most preferably among the compounds of formula (III), the metal complex is lithium 8-hydroxyquinolinolate known also as lithium quinolate or LiQ.

Further preferred, the additional electron injecting material can be selected from:

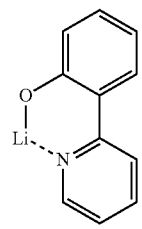

-continued

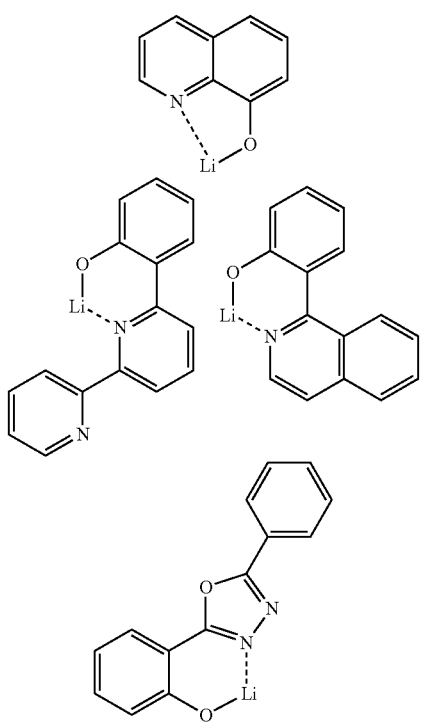
D1

Also preferred are 2,3-diphenyl-5-hydroxyquinoxalinolato lithium, cesium quinolate, potassium quinolate, rubidium quinolate. Additional information of such materials can be found in Jpn. J. Appl. Phys. 45 (2006) pp. L1253-L1255; Liang, Journal of Materials Chemistry v.13, pp. 2922-2926 (2003); Pu et al, 10, pp-228-232, Organic Electronics (2009).

Another preferred class of ETL additives are compounds having general formula (IV)

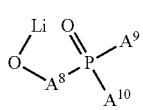
Formula (IV)

wherein $A^8$ is a $C_6$-$C_{20}$ arylene and each of $A^9$-$A^{10}$ is independently selected from a $C_6$-$C_{20}$ aryl, wherein the aryl or arylene may be unsubstituted or substituted with groups comprising C and H or with a further LiO group, provided that the given C count in an aryl or arylene group includes also all substituents present on the said group.

These compounds are described in patent application PCT/EP2012/074127. This class of dopants is represented by compound D2

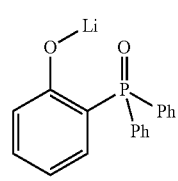
D2 wherein Ph is phenyl.

Still another preferred class of ETL additives are compounds having general formula (V)

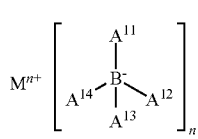
Formula (V)

wherein M is a metal ion, each of $A^{11}$-$A^{14}$ is independently selected from H, substituted or unsubstituted $C_6$-$C_{20}$ aryl and substituted or unsubstituted $C_2$-$C_{20}$ heteroaryl and n is valence of the metal ion.

Preferably, n is 1 or 2. More preferably, M is an alkaline metal or an alkaline earth metal. Most preferably, M is Li or Mg. These compounds are described in patent application PCT/EP2012/074125. This class of dopants is represented by compound D3

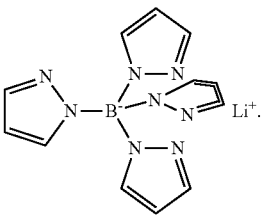
D3

It is preferred that the weight ratio of metal salt or metal complex additive: compound of the formula (I) in the electron transporting layer is 1:1 or less.

EXAMPLES

1. Device Preparation

Diodes

Bottom electrodes were evaporated on glass substrates (100 nm Al, 40 nm Au) under ultra-high vacuum conditions. The substrates were then immersed into the 1 mM THF reaction solution of bis(1,2,3-triazol-4-yl)-disulfide (TAD) and F4TCNQ for 5 min, rinsed with pure THF and blow-dried in a nitrogen stream. To investigate the effect of annealing, some substrates were heated to 40° C. in a nitrogen glovebox after the assembly process. Finally, 100 nm pentacene and 100 nm Al were evaporated on top. For comparison, reference samples without SAM treatment are processed as well. Furthermore some gold electrodes are covered with 2 nm F6TCNNQ prior to pentacene evaporation, which is commonly used to improve injection and which sets the benchmark for our SAM approach.

After encapsulation, current-voltage characteristics were measured by a source measurement unit (Keithley 2400). Since the interface aluminum/pentacene is considered to act as a Schottky-barrier, a diode like behavior of the devices is expected. While the reverse behavior of these diodes is governed by the aluminum/pentacene barriere, the forward performance is basically a result of the transport properties of pentacene as well as of the injection of charges from gold into the semiconductor material. Moreover, in analogy to OTFT observations where the device performance is limited by injection for a channel length<10 μm, it is expected that the forward direction of our diodes is restricted by the charge carrier injection rather than the pentacene itself.

OFETs

Readily structured bottom-gate, bottom-contact transistor-test chips (IPMS Generation 5, channel length L=20 μm, channel width W=10 mm, gate oxide=230 nm SiO$_2$) with gold source- and drain-electrodes are used for this purpose.

Prior to the SAM treatment, the chips were cleaned in acetone, ethanol and deionized water for 5 min in an ultrasonic bath. Following on that, oxygen plasma treatment for 10 min was provided to the sample. After this treatment, the chip was instantly immersed into a 1 mM THF reaction solution of TAD and F4TCNQ for 5 min (first 30 s in an ultra-sonic bath and then 5 min soaking), rinsed with pure THF and blow-dried in a nitrogen stream. In order to prepare the reaction solution, 50 mg F4TCNQ (0.18 mmol, 2 eq) and 18 mg TAD (0.09 mmol, 1 eq) were dissolved under nitrogen atmosphere in 9 mL tetrahydrofuran in a 25 mL flask. Presence of stabilizers in the used THF was avoided. A clear green solution formed was stirred overnight at rt. 1 mL volume of the prepared solution was diluted with 9 mL THF without stabilizers. The SAM-treated chips were dried for 20 min at 40° C. in a nitrogen atmosphere. A 40 nm thick layer of pentacene was then deposited on the SAM-treated substrate under ultra-high vacuum conditions. The temperature of the substrate was kept at room temperature.

For better transport properties of the organic semiconductor material, the samples were preferably treated hexamethyldisilazane (HMDS) prior to the above described SAM treatment. In this case, after the plasma treatment, the sample was dipped first into 10 mM HMDS solution in toluene for 30 s (ultra sonic bath) and further soaked for 5 min in the HMDS solution. Afterwards, the sample was washed with pure toluene and dried under nitrogen stream. Subsequently, the treatment with the injection layer material as described above was employed. It is believed that HMDS makes the insulator layer more hydrophobic and thus improves regularity of pentacene layer deposited on it.

Figure 4:
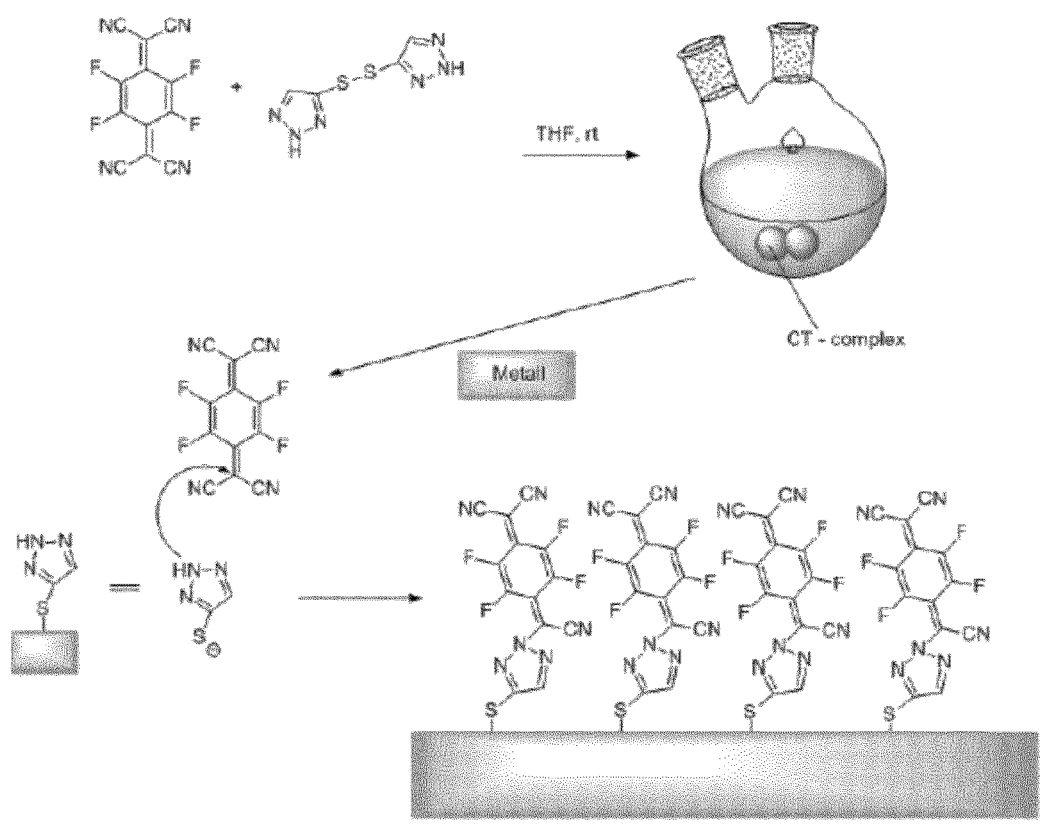
FIG. 4 shows schematically the formation of a coloured complex in the solution of bis(1,2,3-triazol-4-yl)disulfide and F4TCNQ in tetrahydrofuran (THF), dissociation of the disulfide bond in the anchor group, and formation of the inventive molecule anchored by a covalent sulfide bond to the metal surface.

FIG. 4 shows an example of structure of the inventive compound which can be prepared and anchored on a metal surface as a molecular layer by the inventive process.

Figure 5:
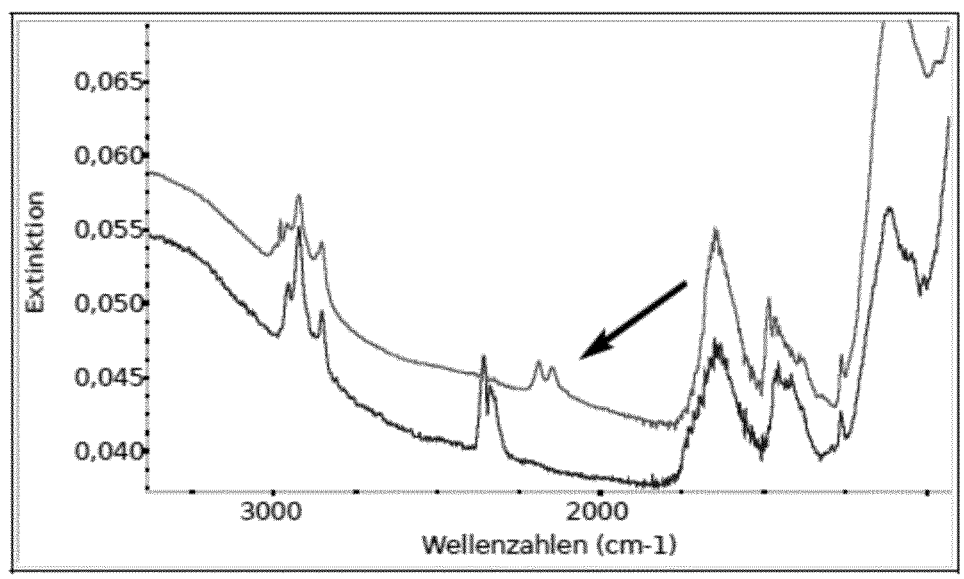
FIG. 5 shows a Fourier-Transformation Infrared Spectra (FTIR) evidence for the formation of the product schematically shown in FIG. 4, on a gold surface.

FIG. 5 shows comparison of FTIR-ATR spectra of the untreated gold electrode (bottom line) and of the same electrode after treatment with the TAD+F4TCNQ THF solution as described in the device preparation example above (top line). The arrow shows double peak belonging to stretching vibrations of nitrile groups in the anchored inventive compound.

Figure 6:
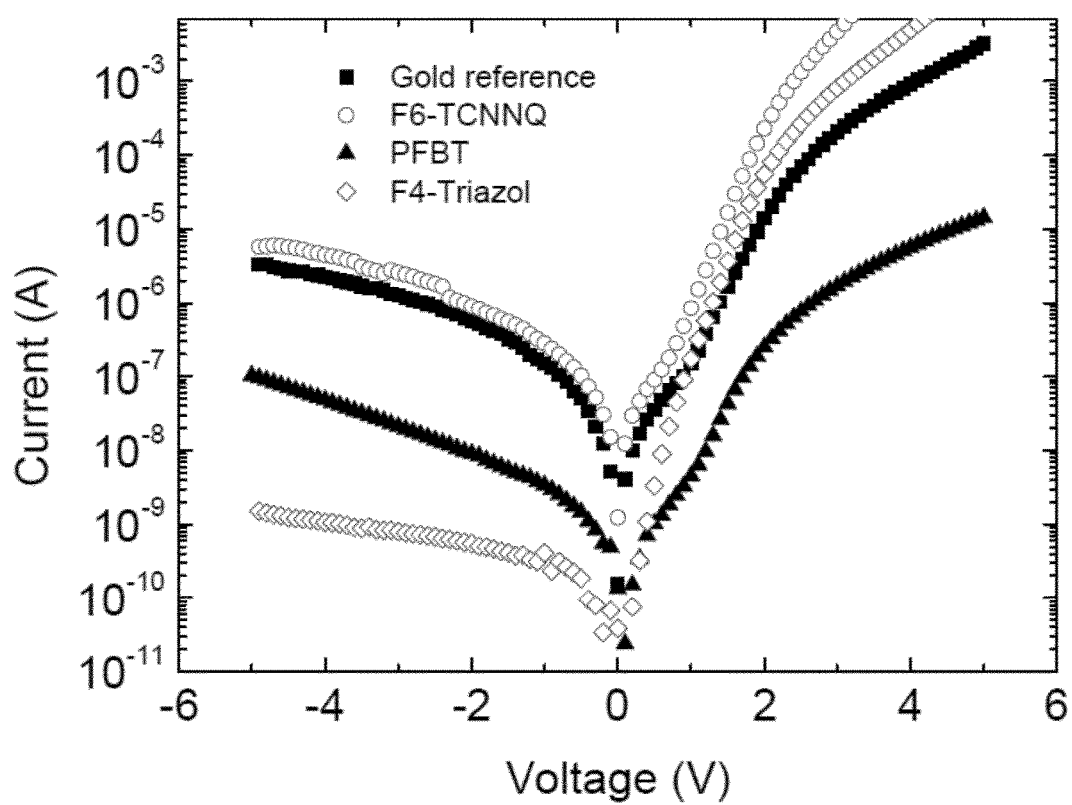
FIG. 6 shows a comparison of the current-voltage curves of comparative and inventive diodes.

FIG. 6 shows I-V (current-voltage) curves measured in above described pentacene diode provided with the inventive monolayer schematically depicted on the FIG. 4 (empty diamonds assigned F4-Triazol) in comparison with analogous devices provided with a monolayer of perfluorobenzenethiole (PFBT, full triangles), vapour-deposited 2 nm layer of F6-TCNNQ (empty circles) and with an unmodified gold electrode (full squares). It is clearly seen that the device comprising the inventive anchored thin molecular layer had superior performance.

Figure 7:
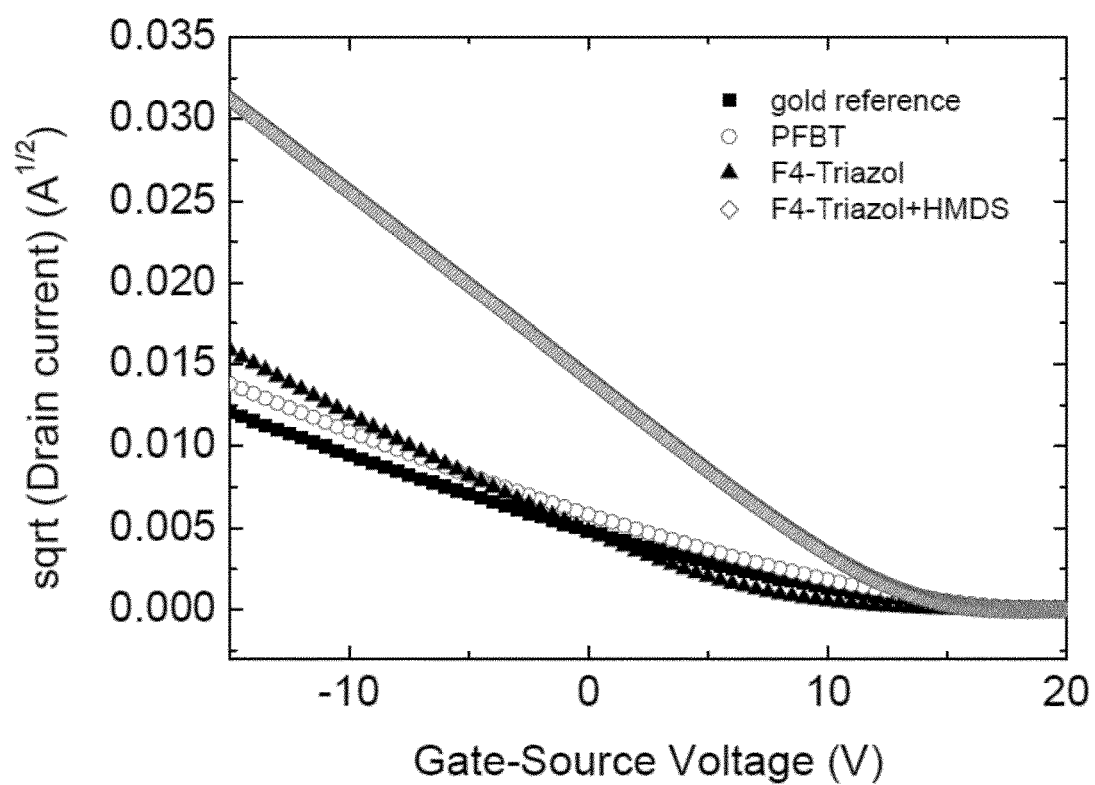
FIG. 7 shows a comparison of the current-voltage curves of comparative and inventive OFETs.

FIG. 7 shows I-V (current-voltage) curves measured in above described pentacene OFET provided with the inventive anchored thin molecular layer schematically depicted on the FIG. 4 (F4-Triazol, full triangles and empty diamonds), in comparison with equivalent devices comprising pentafluorobenzenethiole SAM (PFBT, empty circles) or untreated gold electrode.

The skilled in the art can recognize the features disclosed in the foregoing description, in the claims_and the drawings which may, both separately and in any combination thereof, be material for realizing the invention in diverse forms thereof.

SYMBOLS, ABBREVIATIONS, TERMS

OLED—organic light emitting diode
OFET—organic field effect transistor
OTFT—organic thin film transistor
ETM—electron transport material
ETL—electron transport layer
EIL—electron injecting layer
HTL—hole transporting layer
HIL—hole injecting layer
EIM—electron injecting material
ETM—electron transporting material
EWG—electron withdrawing group
HTM—hole transporting material
HIM—hole injecting material
EML—light emitting layer
p:HTL—p-doped HTL
n:ETL—n-doped ETL
TAD—bis(1,2,3-biazol-4-yl)-disulfide
F4TCNQ—2,3,5,6-tetrafuoro-7,7,8,8-tetracyanoquinodimethane
F6TCNNQ—1,3,4,5,7,8-hexafluoronaphtalene-2,6-diylidene-dimalononitrile
THF—tetrahydrofuran
HMDS—hexamethyldisilazane
PFBT—perfluorbenzenethiol
w/w—by weight
v/v—by volume
mol.—molar (e.g. percent)
eq—equivalent
rt—room temperature
LiQ—lithium 8-hydroxyquinolinolate
HAT—hexaazatriphenylene
HATCN—hexaazatriphenylene hexacarbonitrile
LEL—light emitting layer
CGL—charge generating layer
SAM—self assembling monolayer
FTIR-ATR—Fourier-transformation infrared (spectroscopy)—attenuated total reflection
IP—ionisation potential
EA—electron affinity
UPS—ultraviolet photoelectron spectroscopy
IPES—inverted photoelectron spectroscopy
HOMO—highest occupied molecular orbital
LUMO—lowest unoccupied molecular orbital
VTE—vacuum thermal evaporation
IPMS—Institut für photonische Mikrosysteme

The invention claimed is:

1. An electronic or optoelectronic device comprising at least one inorganic surface covered at least partly by an organic layer, wherein the organic layer comprises a compound comprising
   i) at least one anchor group anchoring the compound to the inorganic surface,
   ii) at least one first functional moiety comprising
      a) a first aromatic heterocycle comprising at least one nitrogen atom in an aromatic ring, or
      b) a first aromatic or heteroaromatic ring substituted with at least one secondary or tertiary amine group, and
   iii) at least one methylidenyl group,
   wherein at least one of the nitrogen atoms of the first aromatic heterocycle, the secondary amine group, or the tertiary amine group is directly attached by a single bond to the methylidenyl group, and wherein the anchor group is attached to the functional moiety either directly or by a spacer.

2. The device according to claim 1, wherein the methylidenyl group directly attached by a single bond to at least one of the nitrogen atoms of the first aromatic heterocycle, the secondary amine group, or the tertiary amine group is substituted with an electron withdrawing group or with a second functional moiety, wherein the second functional moiety comprises
   a) a second aromatic heterocycle comprising at least one nitrogen atom in an aromatic ring, or
   b) a second aromatic or heteroaromatic ring substituted with at least one secondary or tertiary amine group,
   wherein the second functional moiety is attached to the methylidenyl group through a single bond between the methylidenyl group and at least one nitrogen atom of the second aromatic heterocycle, the secondary amine group of the second aromatic or heteroaromatic ring, or the tertiary amine group of the second aromatic or heteroaromatic ring.

3. The device according to claim 2, wherein the electron withdrawing group is a cyano group.

4. The device according to claim 1, wherein the inorganic surface is a metal surface, and the anchor group comprises at least one chalcogen atom selected from S, Se, or Te having an oxidation degree (-II), (-I), or 0.

5. The device according to claim 4, wherein the metal surface comprises at least one metal selected from Group 8, 9, 10, or 11 of the Periodic Table.

6. The device according to claim 4, wherein the metal surface comprises a metal selected from Cu, Ag, Au, Pd, or Pt.

7. The device according to claim 1, wherein the anchor group is selected from —SH or $S_x$—, wherein x is an integer selected from 1, 2, 3, 4, or 5.

8. The device according to claim 1, wherein the anchor group is directly attached to the first aromatic heterocycle or the first aromatic or heteroaromatic ring of the functional moiety.

9. The device according to claim 1, wherein the at least one first functional moiety is a five membered aromatic heterocycle comprising nitrogen.

10. The device according to claim 1, wherein the at least one first functional moiety is selected from azole, diazole, triazole, or tetrazole.

11. The device according to claim 1, wherein the at least one first functional moiety is substituted with at least one electron withdrawing group.

12. The device according to claim 11, wherein the electron withdrawing group is independently selected from —F, —Cl, —CN, halogenated alkyl, halogenated aryl, or halogenated heteroaryl.

13. The device according to claim 1, wherein the at least one methylidenyl group is conjugated with at least one pi-bond of an other conjugated pi-electron system.

14. The device according to claim 13, wherein the other conjugated pi-electron system is substituted with at least one electron withdrawing group, is electron withdrawing itself, or a combination thereof.

15. The device according to claim 13, wherein the other conjugated pi-electron system is a quinoid, truxequinone, or radialene pi-electron system.

16. A compound comprising:
   i) at least one functional moiety comprising
      a) an aromatic heterocycle comprising at least one nitrogen atom in an aromatic ring, or
      b) an aromatic or heteroaromatic ring substituted with at least one secondary or tertiary amine group,
   ii) at least one anchor group comprising at least one chalcogen atom selected from S, Se, or Te in the oxidation degree (-II), (-I) or 0, the anchor group being attached to the functional moiety either directly or by a spacer,
   iii) at least one methylidenyl group, and
      wherein at least one nitrogen atom in the aromatic ring of the aromatic heterocycle, the secondary amine group, or the tertiary amine group is directly attached by a single bond to the methylidenyl group.

* * * * *